United States Patent [19]
Sasaki et al.

[11] Patent Number: 5,736,349
[45] Date of Patent: *Apr. 7, 1998

[54] MAGNETIC PARTICLE AND IMMUNOASSAY USING THE SAME

[75] Inventors: Motohiro Sasaki; Masahiko Matsukawa, both of Kanagawa-ken; Katsuaki Yoshioka, Tokyo; Makoto Anan, Chiba-ken; Mitsuo Isomura, Tokyo; Yoshihiro Ashihara, Tokyo; Masahisa Okada, Tokyo, all of Japan

[73] Assignees: Nippon Paint Co., Ltd., Osaka-fu; Fujirebio Inc. (Fujirebio Kabushiki Kaisha), Tokyo, both of Japan

[*] Notice: The term of this patent shall not extend beyond the expiration date of Pat. No. 5,320,944.

[21] Appl. No.: 440,175

[22] Filed: May 12, 1995

Related U.S. Application Data

[63] Continuation of Ser. No. 111,678, Aug. 25, 1993, abandoned, which is a continuation-in-part of Ser. No. 965,612, Oct. 22, 1992, Pat. No. 5,320,944, which is a continuation of Ser. No. 590,834, Sep. 28, 1990, abandoned.

[30] Foreign Application Priority Data

Sep. 29, 1989 [JP] Japan ................. 1-252051
Aug. 31, 1992 [JP] Japan ................. 4-253455

[51] Int. Cl.⁶ .............. G01N 33/553; C07K 17/14
[52] U.S. Cl. .............. 435/7.94; 436/526; 436/532; 436/533; 436/534; 530/391.1
[58] Field of Search .............. 435/7.94; 436/526, 436/532, 533, 534; 530/391.1

[56] References Cited

U.S. PATENT DOCUMENTS

| | | | |
|---|---|---|---|
| 4,177,253 | 12/1979 | Davies | 424/1 |
| 4,911,957 | 3/1990 | Oishi et al. | 427/443.1 |
| 5,215,782 | 6/1993 | Yoshioka et al. | 427/132 |
| 5,320,944 | 6/1994 | Okada et al. | 435/7.94 |

FOREIGN PATENT DOCUMENTS

| | | |
|---|---|---|
| 0234083 | 9/1987 | European Pat. Off. |
| 420186 | 4/1991 | European Pat. Off. |
| WO89/04373 | 5/1989 | WIPO |

*Primary Examiner*—Mary E. Ceperley
*Attorney, Agent, or Firm*—Jordan and Hamburg

[57] ABSTRACT

There are disclosed a magnetic particle for an immunoassay method, which comprises a core and a coating layer formed on the surface of the core wherein said core comprises an organic polymer matrix and said coating layer comprises a mixed crystal ferrite represented by the formula:

$$M_xFe_{(3-x)}O_4$$

wherein M represents at least one metal selected from the group consisting of Mn, Ni, Zn, Co, Cu, Mg, Sn, Ca and Cd, and x is a number satisfying the relation: $0<x<3$, and an antigen or an antibody is bound onto the surface of the coating layer and wherein said particle has a particle size of 0.03 to 10 μm, and an immunoassay method using the same.

15 Claims, 7 Drawing Sheets

MAGNETIC PARTICLE AND IMMUNOASSAY USING THE SAME

The application is a continuation of application Ser. No. 08/111,678, filed Aug. 25, 1993, now abandoned, which is a continuation-in-part of U.S. patent application Ser. No. 07/965,612, filed Oct. 22, 1992, now U.S. Pat. No. 5,320,944, which is a continuation of U.S. patent application Ser. No. 07/590,834, filed Sep. 28, 1990, now abandoned.

FIELD OF THE INVENTION

This invention relates to a magnetic particle for an immunoassay and an immunoassay using the same, more specifically to a magnetic particle for an immunoassay having a specific particle size and a specific saturation magnetization which comprises a core comprising an organic polymer material, a coating layer of a mixed crystal ferrite comprising a specific metal oxide formed on the surface of the core, and an antigen or an antibody bound onto the surface of the coating layer, and an immunoassay using the same.

BACKGROUND OF THE INVENTION

In an immunoassay, particularly in an enzyme immunoassay, it is advantageous to employ latex particles with smaller particle sizes in a solid phase in place of beads having larger particle sizes since an immuno reaction can be carried out with high sensitivity. However, when particles having smaller particle sizes are employed, for effecting B/F (Bound/Free) separation, a centrifugal separator should be used or filtration by using a filter should be done.

Thus, it cannot help saying that the method is simple. As a method for effecting B/F separation effectively and simply, there has been proposed a method in which magnetic particles having smaller particle sizes are employed. As such methods, there have been known an immunoassay using particles having particle sizes of 1.0 to 10.0 µm wherein a silane is coated on magnetite as a core (see Japanese Provisional Patent Publications No. 141670/1980 and No. 122997/1975), an immunoassay using particles having particle sizes of 0.1 to 1.5 µm wherein a silane is coated on a magnetic metal oxide as a core (see Japanese Provisional Patent Publication No. 1564/1985) and an immunoassay using particles having particle sizes of 0.2 to 3 µm wherein a silane is coated on an organic material as a core (see Japanese Provisional Patent Publication No. 115862/1991).

Further, as a method for preparing magnetic particles in which ferrite particles are bound onto the surface of a core particle, Japanese Provisional Patent Publication No. 65085/1988 discloses a method using a principle of ferrite plating. In this method, however, a by-product of an oxide is likely caused so that reproducibility of saturation magnetization is not so good. Furthermore, according to Japanese Provisional Patent Publication No. 237019/1991 (which corresponds to U.S. Pat. No. 5,215,782), magnetic particles coated with ferrite can be obtained by adding a ferrous ion aqueous solution, an oxidizing agent aqueous solution and a pH controller to magnetic particles while maintaining a relation between a pH and oxidation-reduction potential of the pH-oxidation-reduction potential graph within a specific range, and a saturation magnetization of the resulting magnetic particles can be controlled to a desired range with less causing by-products. However, these magnetic particles have a large residual saturation magnetization and once magnetic response is carried out, agglomeration of the magnetic particles occurs due to their magnetism. Also, when magnetic separation is once carried out with respect to the conventional magnetic particles, a residual magnetization occurs and even after they are dispersed again, agglomeration of the magnetic particles is admitted. Thus, if a reagent for measurement is prepared by applying magnetic separation procedure to the magnetic particles, agglomeration of the particles occurs so that a reagent having a predetermined particle size cannot be obtained. Furthermore, when the procedure of effecting immunoassay and magnetic separation is repeated, dispersibility and floating property are lowered so that there are problems that measured values are lowered and an assay with good reproducibility cannot be carried out. Further, in conventional particles, if an immuno reaction is once carried out, there are drawbacks that the particles are agglomerated due to influence of residual magnetism, whereby dispersibility and floating property are lowered for a long time of one hour or longer. When an immuno reaction is effected twice by using conventional particles, there are drawbacks that dispersibility and floating property during the second reaction are lowered, whereby the obtained results are fluctuated or intensities of signals are lowered.

Further, as particles using an organic material as a core, there has been used particles having a diameter of 3 µm or less in order to ensure floating property during an immuno reaction and a diameter of 0.2 µm or more in order to increase magnetic separating efficiency. However, precipitation of said particles is observed during an immuno reaction so that said particles are not optimum particles to be used for an immunoassay.

SUMMARY OF THE INVENTION

The present inventors have studied intensively to overcome these problems and as a result, they have found that when mixed crystal ferrite-coated magnetic particles having an average particle size of 0.03 to 10 µm which comprises a core comprising an organic polymer matrix and a coating layer of a mixed crystal ferrite comprising specific metals at a specific composition ratio formed on the surface of the core are used, it is possible to obtain particles having high magnetic responsibility at magnetic separation and high dispersion floating property even after washing operation after an immuno reaction without lowering floating property during the immuno reaction, to accomplish the present invention.

That is, the present invention is a magnetic particle for an immunoassay method, which comprises a core and a coating layer formed on the surface of the core wherein said core comprises an organic polymer matrix and said coating layer comprises a mixed crystal ferrite represented by the formula:

$$M_xFe_{(3-x)}O_4$$

wherein M represents at least one metal selected from the group consisting of manganese, nickel, zinc, cobalt, copper, magnesium, tin, calcium and cadmium, and x is a number satisfying the relation: $0<x<3$, preferably $0.05<x<1.5$, and an antigen or an antibody is bound onto the surface of the coating layer and wherein said particle has a particle size of 0.03 to 10 µm.

BRIEF DESCRIPTION OF THE DRAWING

FIG. 6 (a) is a view showing time course curves of signal values of conventional magnetite-coated particles of Comparative example 8 and mixed crystal ferrite-coated particles of Example 8 when stirring is not carried out during the first immuno reaction and stirring is carried out during the second immuno reaction; and FIG. 6 (b) is a view showing time course curves of signal values of conventional magnetite-coated particles of Comparative example 8 and mixed crystal ferrite-coated particles of Example 8 when stirring is carried out during the first immuno reaction and the second immuno reaction.

DESCRIPTION OF THE PREFERRED EMBODIMENTS

In the following, the present invention will be described in more detail.

The magnetic particles for an immunoassay of the present invention can be prepared by using an organic polymer material (or matrix) as a core and subjecting it to an iron oxide type mixed crystal ferrite coating, and then binding an antigen or an antibody to the resulting coated particles.

As the organic polymer material which can be used, there may be used a polymer comprising at least one monomer selected from the group consisting of styrenes, acrylates and methacrylates.

Examples of the styrene type monomer may include styrene, α-methylstyrene, p-methylstyrene, and derivatives thereof.

Examples of the acrylate type monomer may include methyl acryalte, 2-hydroxyethyl acrylate, 2-hydroxypropyl acrylate, 2-acrylamido-2-methylpropane sulfonic acid, ethyl acrylate, n-butyl acrylate, isobutyl acrylate, 2-ethylhexyl acrylate, acrylamide, glycidyl acrylate and methylglycidyl acrylate.

Examples of the methacrylate type monomer may include methyl methacrylate, 2-hydroxyethyl methacrylate, 2-hydroxypropyl methacrylate, 1-methyl-2-hydroxyethyl methacrylate, glycerol monomethacrylate, 2-sulfoethyl methacrylate, acid phosphoxyethyl methacrylate, 3-chloro-2-acid phosphoxypropyl methacrylate, acid phosphoxypropyl methacrylate, ethyl methacrylate, n-butyl methacrylate, isobutyl methacrylate, 2-ethylhexyl methacrylate, lauryl methacrylate, cyclohexyl methacrylate, methacrylamide, glycidyl methacrylate and methylglycidyl methacrylate. And as the other monomers, an acidic monomer such as an acrylic acid and a methacrylic acid may be used. Further, a bi-functional monomer used as a cross-linking agent such as ethylene glycol dimethacrylate (EGDM) and neopentyl glycol dimethacrylate (NPGDM) may be used.

As the method of polymerization using these monomers in order to obtain the polymer, the emulsion polymerization and the multistage emulsion polymerization can be used. As the emulsion polymerization method, there have been known the method in which polymerization is carried out by charging whole monomer composition at one time; the monomer addition method in which a part of monomers and other components than the monomers are prepolymerized and then polymerization is further carried out while continuously adding the remaining monomers to the prepolymer; and the emulsion addition method in which components for polymerization are previously emulsified and a part of the emulsion is prepolymerized, and then remaining emulsions are continuously added to proceed the polymerization. Also, the multistage emulsion polymerization method in which seed latex particles are stepwisely grown without generating new latex particles has been known. These polymerization methods may be selected in consideration of characteristics of monomers, difficulty of removing heat of polymerization, and an average particle size and a particle size distribution of a latex.

For effecting these polymerization reactions, an organic peroxide type initiator such as benzoyl peroxide, lauroyl peroxide, cumen hydroperoxide, di-t-butylperoxide and acetyl peroxide and a nitrile type initiator such as α,α'-azobisisobutyronitrile have been used as a radical polymerization initiator.

Also, a compound which utilizes pyrolysis, such as potassium persulfate, ammonium persulfate and hydrogen peroxide may be used. Further, a redox type polymerization catalyst may be employed. As an emulsifier to be used for the emulsion polymerization, there may be mentioned an ionic active agent such as an anionic active agent, a cationic active agent, an amphoteric active agent and a nonionic active agent.

Next, mixed crystal ferrite coating is carried out to the organic polymer material obtained by the method as mentioned above to form a mixed crystal ferrite-coated particle.

The ferrite coating is carried out in an aqueous solution containing the organic polymer particles. In the aqueous solution are supplied ferrous ions which are essential for forming ferrite coatings and metal ions of at least one metal other than iron selected from the group consisting of manganese, nickel, zinc, cobalt, copper, magnesium, tin, calcium and cadmium (hereinafter sometime referred to as "mixed crystal-forming metal ions"). The ferrous ions and other metal ions are supplied in the aqueous solution in the form of a salt such as hydrochloride ($FeCl_2$), sulfate ($FeSO_4$) and acetate ($Fe(OCOCH_3)_2$), and a hydrate thereof. As to manganese, cobalt and other metals, corresponding salts and hydrates thereof to the above can be exemplified. For example, when iron and manganese ions are used, iron-manganese mixed crystal ferrite ($Mn_xFe_{3-x}O_4$) can be obtained, when iron and nickel ions are used, iron-nickel mixed crystal ferrite ($Ni_xFe_{3-x}O_4$) can be obtained, and mixed crystal ferrite using iron and plural kinds of metal ions may be also useful. These mixed crystal-forming metal ions are supplied in the aqueous solution in the form of water-soluble salts.

In the present invention, formation of ferrite coatings on the surface of an organic polymer particle can be started by adding to a deoxidized dispersion containing the organic polymer particles, the ferrous ions, a mixed crystal-forming metal ion and an oxidizing agent each in the form of an aqueous solution separately or in any combination. Examples of the oxidizing agent may include nitrites, nitrates, hydrogen peroxide, organic peroxides, perchlorates and oxygen-dissolved water.

A pH of the aqueous solution can be optionally selected depending on the kinds of anions and metal ions present in the aqueous solution and can be controlled, but preferably in the range of 6 to 11, more preferably 7 to 10. For stabilizing the pH, a buffer such as ammonium acetate or a salt of carbonate or borate having a buffering effect may be added.

A temperature to carry out the reaction of the present invention may be in the range of the boiling point of the aqueous solution or lower, but the reaction is preferably carried out in the range of 60° C. to 90°C. Also, the reaction is carried out under the substantially deoxidized atmosphere. Under the conditions existing a large amount of oxygen, an oxidization reaction proceeds unnecessarily. More specifically, it is preferred to carry out the reaction under nitrogen atmosphere. Also, oxygen is removed from the aqueous solution to use a deoxidized aqueous solution, similarly.

When the magnetic particle for an immunoassay of the present invention is prepared, it is extremely preferred that particulate materials are firstly suspended in the deoxidized water, and at this time, if necessary, an additive such as a surfactant is added in order to improve wetting of the particulate materials to water. The resulting particulate materials subjected to ferrite coatings are separated by filtration and dried to obtain the desired products.

The mixed crystal ferrite particles in which ammonium acetate is used as a pH stabilizer and the ratio of ferrite and manganese is 2.5/0.5 has a residual mangetization amount ÷a saturation magnetization amount =2.8÷42×100=6.67%, and the mixed crystal ferrite particles in which the ratio of ferrite and manganese is 2.0/1.0 has a residual mangetization amount ÷a saturation magnetization amount =1.3÷31.5× 100=4.1%.

The magnetic particle for an immunoassay to be used in the present invention may be used after it is treated with a polymer and then an antigen or an antibody is bound thereto. As the polymer, there may be used, for example, a silane polymer, nylon (trade name) or a polystyrene. As the method of silane treatment, for example, the acidic aqueous silylation method may be used. It can be accomplished by firstly mixing mixed crystal ferrite-coated particles and silane monomer in an acidic solution and then treating the mixture at room temperature to 95° C. under heating. As the silane monomer to be used, there may be used, for example, an organosilane such as p-aminophenyl-trimethoxysilane, 3-aminopropyltrimethoxysilane, N-2-aminoethyl-3-aminopropyltrimethoxysilane, triamino-functional silane ($H_2NCH_2CH_2$—$NHCH_2CH_2$—$NHCH_2CH_2CH_2$—Si—$(OCH_3)_3$), n-dodecyltriethoxysilane and n-hexyltrimethoxysilane. Further, in order to convert an end amino group of the silane into a carboxylic group, an acid anhydride such as glutaric anhydride, maleic anhydride and succinic anhydride can be reacted to silane-treated particles at room temperature.

Also, for treating with a polyamide, mixed crystal ferrite-coated particles are suspended in a 1% aqueous sodium carbonate solution, an appropriate amount of hexamethylenediamine is dissolved therein, the solution is mixed with 5-fold amounts of a hexane-chloroform mixed solution (3:1) containing 8% Tween 80 (trade name, produced by Kao Corp.), and then mixture is subjected to ultrasonic treatment to form an emulsion. Then, by adding dropwise the same hexane-chloroform mixed solution as mentioned above containing sebacoyl dichloride with an equimolar amount to hexamethylenediamine to the emulsion, the desired particles can be obtained. Also, in the case of a polystyrene, it can be treated by employing the method known in the art. Further, the mixed crystal ferrite-coated particles can be directly coated with a polymer by spraying or dipping in a polymer resin solution such as a polyamide resin (e.g. nylon (trade name)) and a polystyrene.

The present invention relates to magnetic particles for an immunoassay obtained by binding an antigen or an antibody to the mixed crystal ferrite-coated particles obtained by the above method or to the mixed crystal ferrite-coated particles coated with the polymer obtained by further polymer treatment. As the antibody to be used, there may be mentioned, for example, an antibody to a chemical such as theophylline, phenytoin and valproic acid; a low molecular hormone such as thyroxine, estrogen and estradiol; a cancer marker such as CEA and AFP; a virus antigen such as HIV, ATLA and HBV; a high molecular hormone such as TSH and insulin; a cytocain such as IL-1, IL-2 and IL-6; various kinds of gloss factor such as EGF and PDGF; and further a suitable DNA, RNA, etc. of the above viruses. Also, as the antigen to be used, there may be mentioned a virus such as HIV, ATLA and HBV; DNA of the above viruses; a high molecular weight hormone such as insulin add TSH.

As the method of binding an antigen or an antibody to the magnetic particles, the physical adsorption method or the chemical binding method may be employed. The physical adsorption method is carried out by reacting the above particles and an antigen or an antibody in an appropriate buffer solution. As the buffer solution to be used in this reaction, there may be mentioned a phosphate buffer solution, a tris-hydrochloride buffer solution and a carbonate buffer solution. The reaction can proceed easily by mixing both of the components at room temperature to obtain the desired product. Also, as the chemical binding method, the carbodiimide method in the so-called peptide binding method can be employed. Binding can be carried out by, for example, adding an equiamount of a water-soluble carbodiimide to a dispersion containing 0.1 to 5% by weight of silylated particles under acidic conditions (pH 4 to 6), reacting at room temperature for 10 minutes to one hour, removing a supernatant, and then adding 0.01 to 10.0 mg/ml, preferably 0.1 to 5 mg/ml of an antibody or antigen solution. The buffer to be used at this time is preferably a phosphate buffer. Also, as the other chemical binding method, the method in which the reaction is carried out in the presence of a divalent cross-linking reagent such as glutaraldehyde and cyanuric chloride may be employed (see "Peptide Synthesis Method", published by Maruzene K.K., Japan (published in 1975) and "Enzyme Immunoassay Method", published by Kyoritsu Shuppan K.K., Japan, "Protein, Nucleic acid, Enzyme", special issue No. 31 (1987)).

The magnetic particles for an immunoassay produced as mentioned above had a constant particle size. These particles had not changed even when they were preserved in an appropriate protein solution such as BSA and globulin for one year.

The magnetic particles for an immunoassay of the present invention have an average particle size of 0.03 to 10 μm, preferably 0.3 to 5 μm. If the particle size becomes in excess of 10 μm, floating time is short when they are used in immuno reaction so that sufficient reaction cannot be carried out. Also, if it is less than 0.03 μm, magnetic separating efficiency after immuno reaction becomes bad.

The magnetic particles for an immunoassay of the present invention preferably have a saturation magnetization of 1 to 60 emu/g, more preferably 5 to 50 emu/g, most preferably 10 to 40 emu/g. If it exceeds 60 emu/g, the specific gravity becomes large wherein a floating property is lowered, while if it is less than 1 emu/g, magnetically attracting property is lowered.

As the immunoassay method according to the present invention, the radioactive immunoassay method and the enzyme immunoassay method can be used. These assay methods are the immunoassay methods using a label, and an antigen or antibody to be assayed can be assayed by the sandwich method or the competition method.

The enzyme immunoassay method according to the present invention is, for example, to carry out by reacting a magnetic particle for an immunoassay, an enzyme-labelled antibody and a specimen for 10 minutes to 3 hours. A reaction temperature when practicing the reaction is 4° C. to 40° C., preferably 25° C. to 38° C. After washing an unreacted enzyme-labelled antibody, an amount of a ligand of the specimen can be determined by measuring an amount of an antibody-bound enzyme bound to a solid phase, by adding an enzyme substrate and measuring an activity thereof.

An enzyme to be used in the method of the present invention may include peroxidase, alkali phosphatase, β-galactosidase and glucose oxidase.

At this time, it is needless to say that a substrate to be used should be that which is suitable for an enzyme to be used. As such substrates, there may be used, for example, ABTS (2,2'-azino-bis(3-ethylbenzothiazoline-6-sulfonic acid)), luminol-$H_2O_2$ (for peroxidase), 3- (2'-pyro-tricyclo-[3.3.1.1$^{3,7}$]decan)-4-methoxy-4-(3"-phosphoryloxy)phenyl-1,2-dioxetane disodium salt (AMPPD), p-nitrophenylphosphate and methylumbelliferyl phosphate (for alkali phosphatase), 3-(2'-spiroadamantane)-4-methoxy-4-(3"-β-D-galactopyranosyl)phenyl-1,2-dioxetane (AMPGD), p-nitrophenyl-β-O-glactose and methylumbelliferyl-β-O-galactose (for β-galactosidase).

The measurement can be carried out by reacting at room temperature to 40° C. for 1 minute to 18 hours, and then measuring an amount of color, fluorescence or luminescence generated. As the other method, the so-called rate method in which the reaction is carried out at a temperature range of 4° C. to 40° C. under heating may be employed.

Also, the radioimmunoassay method in the immunoassay method is carried out by labelling a radioisotope such as $^{125}I$ in place of the above enzyme label. Operations are quitely the same as the above enzyme immunoassay method except for measuring radioactivity.

Also, radiolabelling of an antigen or an antibody can be readily prepared by the commercially available Bolton-Hunter reagent. It can be prepared by, for example, adding the Bolton-Hunter reagent to an antigen or antibody solution dissolved in a 0.1M sodium hydrogen carbonate aqueous solution, and after 1 to 2 hours, removing the unreacted Bolton-Hunter reagent by using a desalting column of G-25, etc.

In addition, radiolabelling of $^{125}I$ can be easily carried out by employing the chloramine T method or the iododine method. For effecting an immuno reaction, a sample is added to the magnetic particles for an immunoassay of the present invention, and reacted at 4° C. to 40° C., preferably at 20° C. to 38° C. for 1 minute to 18 hours. Thereafter, washing is carried out by a physiological salt solution or distilled water, a radiolabelled antibody is added to the magnetic particles for an immunoassay and reacted at 4° C. to 40° C., preferably 20° C. to 38° C. for 1 minute to 18 hours and washed with a physiological salt solution or distilled water and then its radioactivity is countered. A scintillation counter can be used for the measurement.

Also, the assay method of the present invention may be carried out by the chemiluminescent assay method in which isoluminol or an acridine ester is labelled, or the fluorescent immunoassay method in which fluorescein or rhodamine is labelled. During the procedure, labelling of a labelling substance can be easily carried out by employing the active ester method or the isocyanate method (see "Enzyme immunoassay method" (published by Igaku Shoin, Japan, 1987)).

Similarly, measurement of the antibody can be carried out by using the magnetic particles for an immunoassay of the present invention, mixing these particles with a sample to react them at room temperature to 37° C. for 1 minute to 18 hours, washing with a physiological salt solution or distilled water, then adding a labelled-anti-human immunoglobulin antibody to react at room temperature to 37° C. for 1 minute to 18 hours, washing and measuring the activity of the labelled substance.

The present invention is a magnetic particle for an immunoassay having a specific particle size and a specific saturation magnetization which comprises a core comprising an organic polymer particle, a coating layer of a specific mixed crystal ferrite formed on the surface of the core, and an antigen or an antibody bound onto the surface of the coating layer. These particles may be used as a solid phase of an immunoassay method by which good floating property and dispersibility can be obtained.

EXAMPLES

In the following, the present invention will be explained in more detail by referring to Synthetic examples and Examples. In the followin Synthetic examples and Examples, all the "part"s mean "part by weight" otherwise specifically mentioned.

Synthetic Example 1
(Preparation of Organic Polymer Particle)

In an apparatus for polymerization reaction having a stirrer, a thermometer, a monomer-dropping funnel, a reflux condenser, a heating device and a nitrogen gas inlet tube was charged 230 parts of deionized water, followed by adding 1 part of a mixed monomer (A) composed of styrene, 2-ethylhexyl acrylate and ethyleneglycol dimethacrylate (80/10/10) and 10 parts of a 10% aqueous ammonium persulfate solution at 80° C., and then adding dropwise 99 parts of the above mixed monomer (A) over 3 hours to obtain a latex. When the particles were observed by electron microscope, they were substantially monodispersed and had an average particle size of 0.3 μm.

Synthetic Example 2
(Preparation of Mixed Crystal Ferrite-Coated Particles)

0.9 l of deionized water was charged in a reaction vessel, and into the same reaction vessel was thrown 100 g of a dispersion in which 10 g of the organic polymer particle having an average particle size of 0.3 µm obtained in Synthetic example 1 had been previously dispersed in deionized water. This dispersion was adjusted to pH 8.0 with 0.1 N NaOH and maintained at 70° C. under heating. In the dispersion was supplied at a supplying rate of 60 ml/min a 40% by weight aqueous solution prepared by dissolving 26.1 g of $FeCl_2.4H_2O$ and 13.0 g of $MnCl_2.4H_2O$ in 60.9 g of deionized water and at the same time, supplied at a supplying rate of 0.3 ml/min a 20% by weight sodium nitrite aqueous solution dissolved in deionized water. During this procedure, a pH was maintained at 8.0 constantly. Further, this solution was so controlled that its oxidation reduction potential was maintained at −550 mV constantly. Separation by filtration and water washing of the resulting ferrite-coated particles were repeated to obtain manganese-ferrite-coated organic polymer particles. Also, when part of the sample was freez-dried and the saturation magnetization and the residual magnetization thereof were measured by using VIBRATING SAMPLE B-H CURVE TRACER MODEL BHV-3,5 SERIES manufactured by Riken Denshi Co. at 10K oersted to give the results of 31.5 emu/g and 1.30 emu/g, respectively. The ratio of the residual magnetization and the saturation magnetization at this time was 4.1%.

Example 1
Investigation of Floating Property of Particles

The particles obtained in Synthetic example 2 were dispersed in a 2% BSA solution (0.1M Tris-HCl, 150 mM NaCl, pH: 7.2) to have a concentration of 0.015%. In tubes were charged each 1 ml of the dispersion, one of the tubes were contacted with a magnet having a surface magnetic field of 3000 gauss and then allowed to stand for one day, and the other allowed to stand for one day in a place where there is no surface magnetic field. These particles were washed with a 2% BSA solution once, dispersed in the similar 2% BSA solution, charged in a cell of a spectrophotometer (manufactured by Hitachi Ltd.) and allowed to stand at room temperature.

After 0 minute to 120 minutes, absorptions of supernatants at a wavelength of 660 nm were measured.

Figure 1:
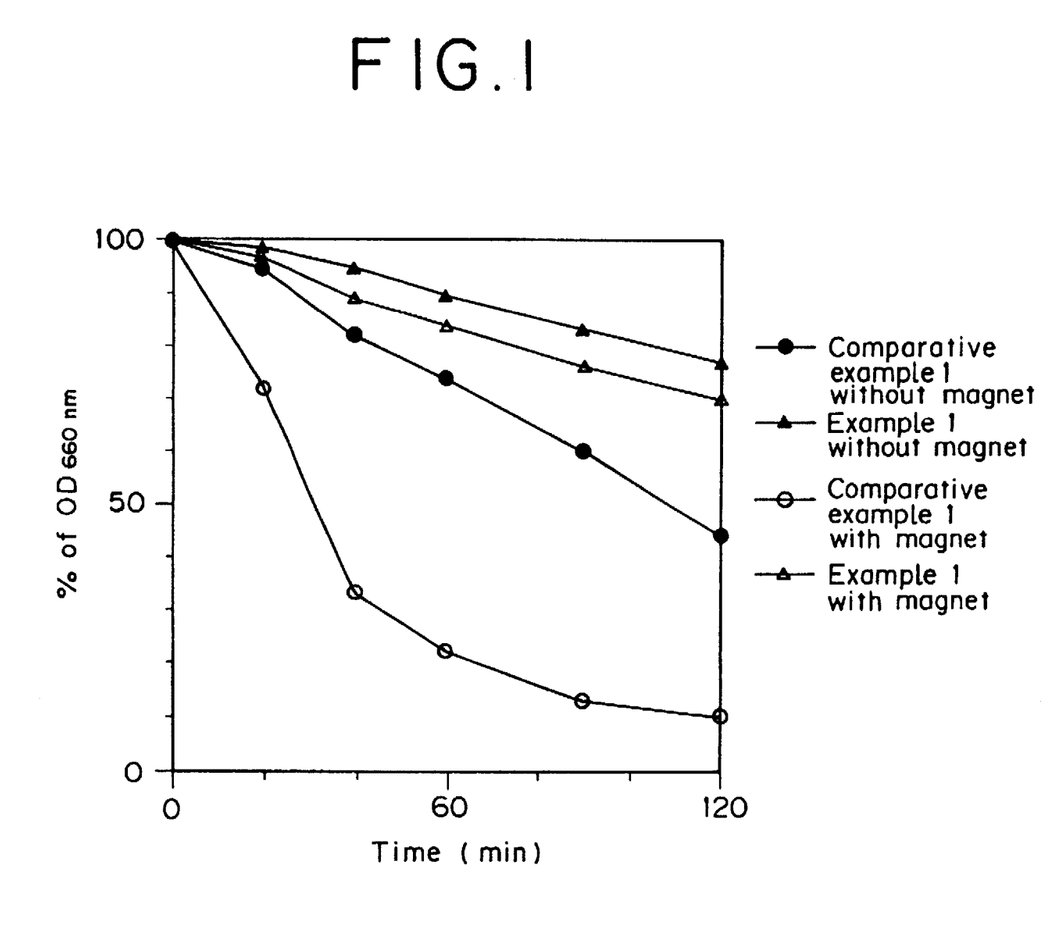
FIG. 1 is a view of comparing turbidities of supernatants when conventional magnetite-coated particles of Comparative example 1 and mixed crystal ferrite-coated particles of Example 1 as such and conventional magnetite-coated particles of Comparative example 1 and mixed crystal ferrite-coated particles of Example 1 which have been attracted by a magnet are charged in cells of a spectrophotometer, respectively, and allowed to stand.

Their relative turbidities are shown in FIG. 1.

Example 2
Comparison of Magnetic Separating Rate of Particles

In tubes were charged 1000 µl of the particles (2% BSA, 0.1M Tris-HCl, 150 mM NaCl, pH: 7.2) used in Example 1, and the tubes were contacted with a magnet having a surface magnetic field of 3000 gauss.

After 0 and 2 minutes of the contact, supernatants were separated charged in cells of a spectrophotometer (manufactured by Hitachi Ltd.), and absorptions of the supernatants at a wavelength of 660 nm were measured.

Figure 2:
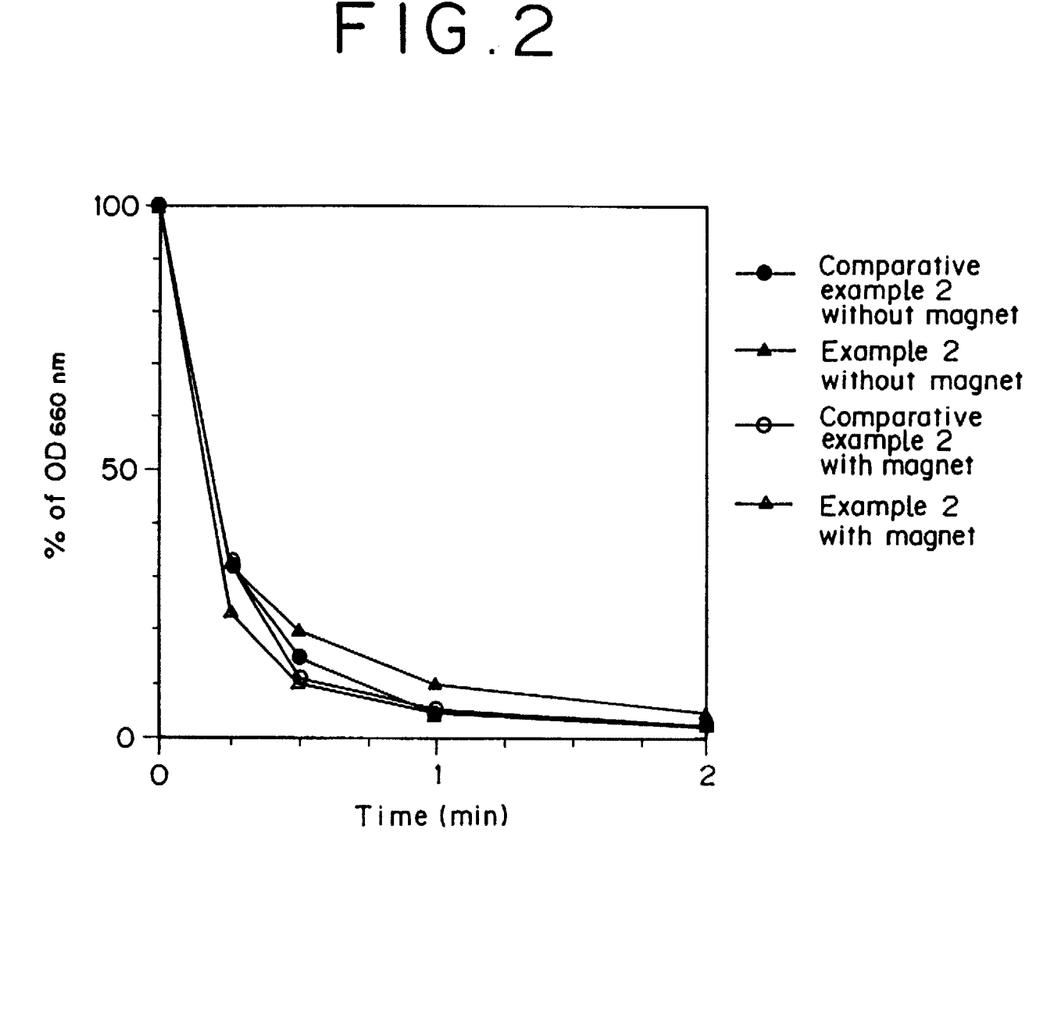
FIG. 2 is a view of comparing turbidities of supernatants when conventional magnetite-coated particles of Comparative example 2 and mixed crystal ferrite-coated particles of Example 2 as such and conventional magnetite-coated particles of Comparative example 2 and mixed crystal ferrite-coated particles of Example 2 which have been attracted by a magnet are further attracted by a magnet, charged in cells of a spectrophotometer, respectively, and allowed to stand.

Their relative turbidities are shown in FIG. 2.

Example 3
Preparation of Carboxylated Particles for Immunoassay

Carboxylated mixed crystal ferrite-coated particles can be obtained by adding 50 ml of 3-aminopropyltriethoxysilane to the manganese-ferrite-coated particles (average particle size of the organic polymer particle: 0.3 µm) of Synthetic example 2 which had been previously washed 5 times for each 60 seconds with distilled water by using an ultrasonic washing machine (Batt type, manufactured by Nippon Seiki Seisakusho K.K.) and further adding 30 ml of glacial acetic acid to react at room temperature for 3 hours, followed by washing and then reacting with glutaric acid anhydride. Glacial acetic acid was added dropwise under ice-cooling and stirring, and washing was carried out each three times with distilled water, methanol and distilled water, and further five times with each 300 ml of a 0.1M sodium hydrogen carbonate solution. The reaction with glutaric acid anhydride was carried out by adding 2.85 g of glutaric acid anhydride to 100 ml of a dispersion containing 5% by weight (0.1M sodium hydrogen carbonate solution) particles and reacting for 10 minutes. After completion of the reaction, the mixture was washed three times with each 300 ml of a 0.1M sodium hydrogen carbonate solution, and further five times with distilled water. This was used as carboxylated particles for an immunoassay.

Example 4
Preparation of Anti-AFP Bound Carboxylated Particles for Immunoassay In 5 ml of 20 mM phosphate buffer (pH 4.5) was dispersed 50 mg of the carboxylated particles for an immunoassay prepared in Example 3, followed by adding 50 mg of water-soluble carbodiimide. After reacting at room temperature for 20 minutes, the supernatant was removed, and 5 ml of an anti-AFP mouse IgG solution (1 mg/ml, 0.02M phosphate buffer solution, pH: 4.5), and the mixture was stirred by an end-over-end mixer. After 2 hours, these particles were washed five times with a 2% BSA solution (0.1M Tris-HCl, 1 mM $MgCl_2$, pH: 7.5) and dispersed in the similar BSA solution to obtain anti-AFP mouse IgG sensitized (bound) carboxylated particles for an immunoassay.

Example 5
Investigation of Floating Property of Particles

The antibody-bound particles prepared in Example 4 were dispersed in a 2% BSA solution (0.1M Tris-HCl, 150 mM NaCl, pH: 7.2) to have a concentration of 0.015%. In two tubes were charged each 1 ml of the dispersion, one of the tubes was contacted with a magnet having a surface magnetic field of 3000 gauss and then allowed to stand for one day, and the other allowed to stand for one day in a place where there is no surface magnetic field. These particles were washed with a 2% BSA solution once, dispersed in the similar 2% BSA solution, charged in cells of a spectrophotometer (manufactured by Hitachi Ltd.) and allowed to stand at room temperature.

After 0 minute to 120 minutes, absorptions of supernatants at a wavelength of 660 nm were measured.

Figure 3:
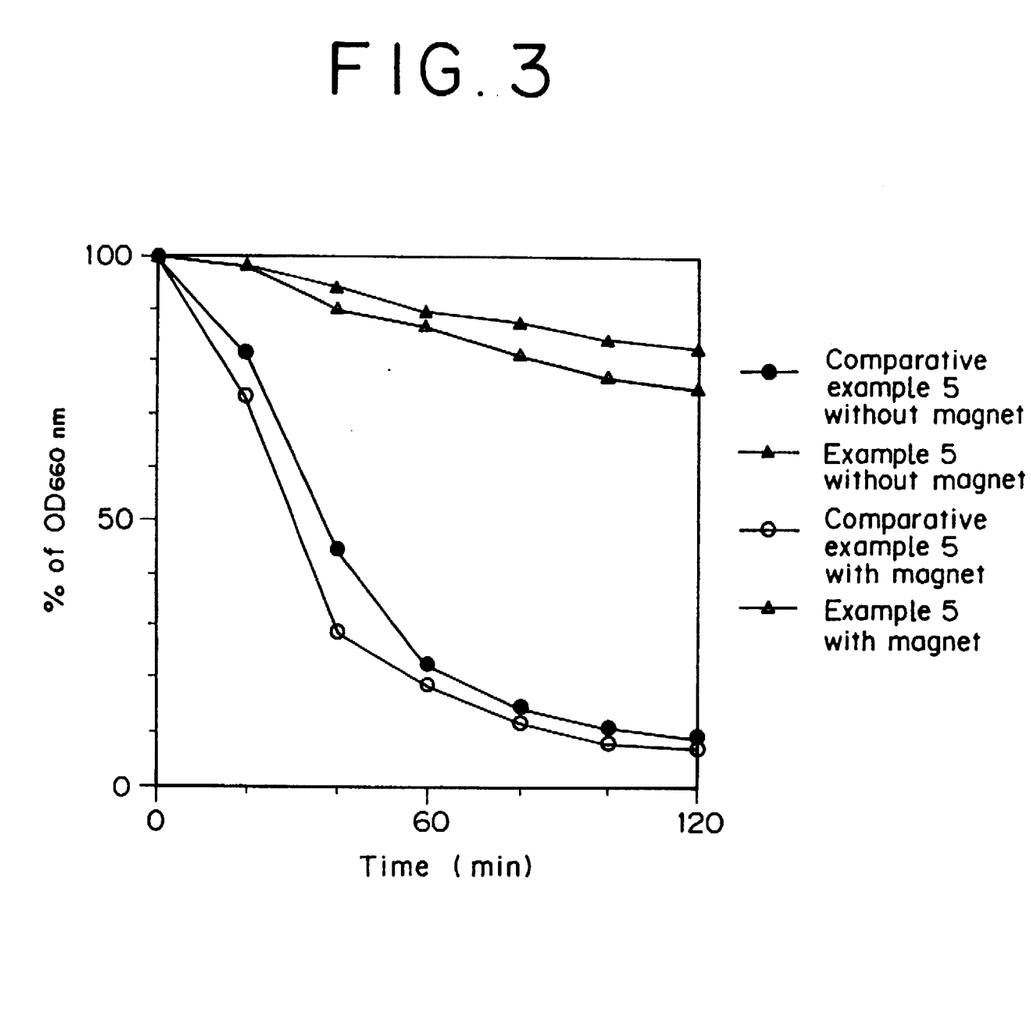
FIG. 3 is a view of comparing turbidities of supernatants when conventional magnetite-coated particles of Comparative example 5 and mixed crystal ferrite-coated particles of Example 5 as such and conventional magnetite-coated particles of Comparative example 5 and mixed crystal ferrite-coated particles of Example 5 which have been attracted by a magnet are charged in cells of a spectrophotometer, respectively, and allowed to stand.

Their relative turbidities are shown in FIG. 3.

Example 6
Comparison of Magnetic Separating Rate of Particles

In tubes were charged 1000 µl of the antibody-bound particles prepared in Example 4 (2% BSA, 0.1M Tris-HCl, 150 mM NaCl, pH: 7.2), and the tubes were contacted with a magnet having a surface magnetic field of 3000 gauss.

After 0 to 2 minutes of the contact, supernatants were each separated and charged in a cell of a spectrophotometer (manufactured by Hitachi Ltd.) and absorptions of the supernatants at a wavelength of 660 nm were measured.

Figure 4:
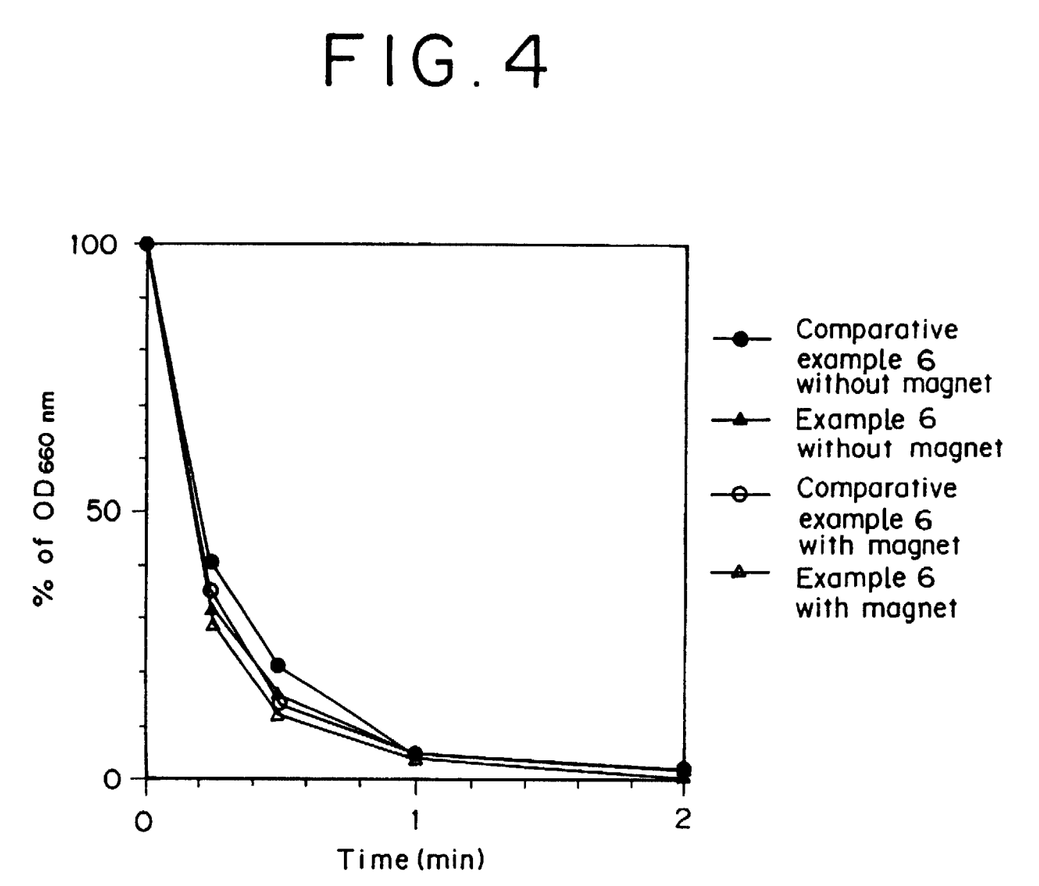
FIG. 4 is a view of comparing turbidities of supernatants when conventional magnetite-coated particles of Comparative example 6 and mixed crystal ferrite-coated particles of Example 6 as such and conventional magnetite-coated particles of Comparative example 6 and mixed crystal ferrite-coated particles of Example 6 which have been attracted by a magnet are further attracted by a magnet, charged in cells of a spectrophotometer, respectively, and allowed to stand.

Their relative turbidities are shown in FIG. 4.

Example 7
AFP Assay Using Anti-AFP Mouse IgG Sensitized Particles for Immunoassay 250 µl of the magnetic particles for an immunoassay coated with anti-AFP mouse IgG prepared in Example 4 was mixed with 10 μl of a sample containing 100 ng/ml of AFP, and the mixture was reacted at 37° C. for 5 to 30 minutes. A tube containing the above mixture was contacted with a magnet having a surface magnetic field of 3000 gauss to attract the particles for an immunoassay and the supernatant was removed by decantation. Thereafter, 1 ml of a 0.04% physiological salt solution was added to the particles and the mixture was stirred. The tube was again contacted with the above mentioned magnet to separate the particles and a supernatant, and the supernatant was removed by decantation. These operations were repeated three times.

Then, to the tube containing the above particles was added 250 μl of alkali phosphatase conjugate (conjugate concentration: 0.1 μg/ml, 0.1M Tris-HCl, 2% BSA, 1 mM MgCl$_2$, 0.1 mM ZnCl$_2$, pH: 7.5) to which anti-AFP Fab' was bound, and the mixture was reacted at 37° C. for 10 minutes. This tube was contacted with the above mentioned magnet to attract the particles for an immunoassay, and the particles were washed by the above mentioned method.

To the tube containing these particles was added 200 μl of a substrate solution (0.1M DEA-HCl, 1 μM MgCl$_2$, 0.1 mM ZnCl$_2$, pH: 10.5) containing 200 μg/ml of AMPPD, and the mixture was reacted at 37° C. for 5 minutes. Thereafter, a sample obtained was measured by a luminometer (manufactured by ALOKA Co.).

Figure 5:
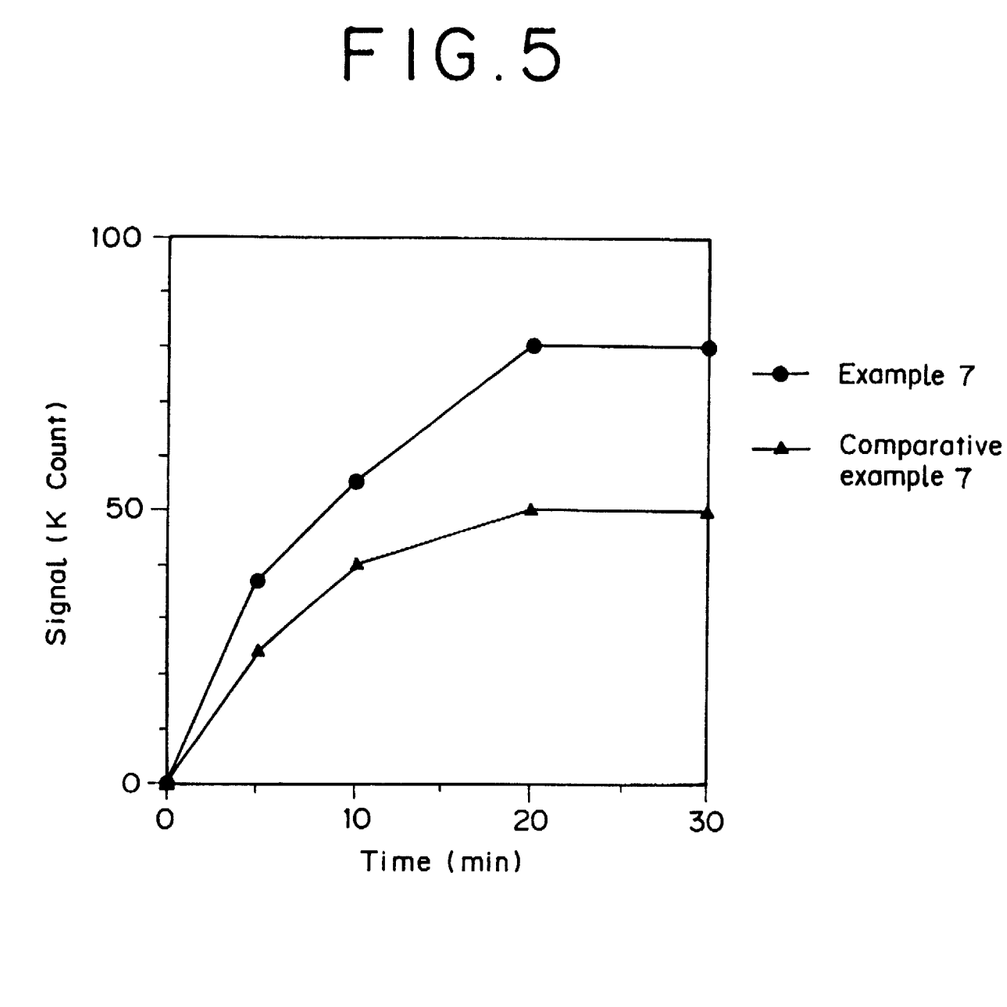
FIG. 5 is a view showing time course curves of signal values of conventional magnetite-coated particles of Comparative example 7 and mixed crystal ferrite-coated particles of Example 7.

Time course curves of signal values are shown in FIG. 5.

S/N ratios of integrated values for 5 minutes are shown in Table 1. An S/N ratio of the assay method using mixed ferrite-coated particles is 1.6 times greater than that of using conventional magnetite-coated particles. Thus, it can be understood that the assay method of using the mixed ferrite-coated particles provides an assay method with higher sensitivity.

TABLE 1

| Particle | Signal | Noise (Blank) | S/N |
|---|---|---|---|
| Mixed crystal ferrite-coated particles | 80.0 | 0.04 | 2000 |
| Particles of Japanese Provisional Patent Publication No. 115862/1991 | 50.0 | 0.04 | 1250 |

Example 8
AFP Assay Using Anti-AFP Mouse IgG-Sensitized Particles for Immunoassay Under Stirring The AFP assay was carried out in the same manner as in Example 7 except for carrying out the first immuno reaction at room temperature for 15 to 60 minutes while stirring or without stirring, and carrying out the second immuno reaction at room temperature for 30 minutes while stirring.

Figure 6:
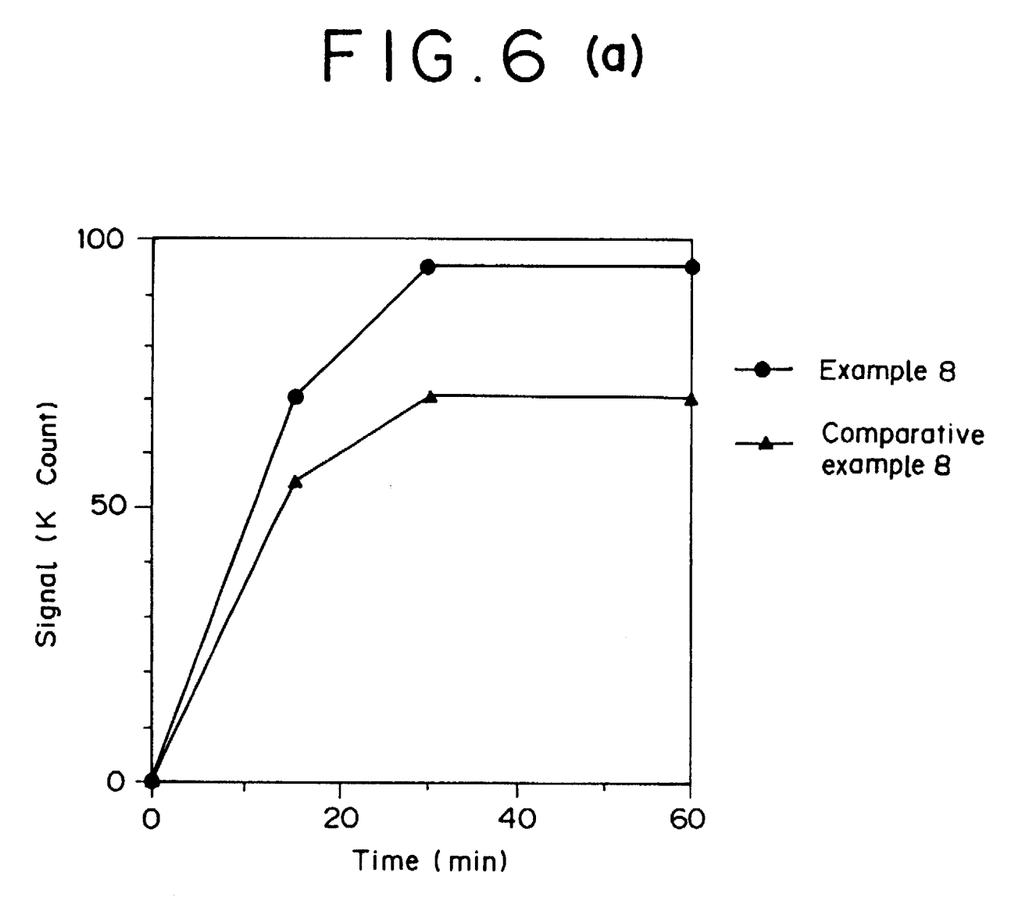

Time course curves of signal values depending on presence or absence of stirring are shown in FIG. 6. In FIG. 6, FIG. 6(a) is without stirring and FIG. 6(b) is with stirring.

Comparative Examples 1, 2, 5, 6, 7 and 8

Procedures were carried out in the same manner as in Examples 1, 2, 5, 6, 7 and 8, respectively, except for using conventional ferrite (magnetite)-coated magnetic particles of Japanese Provisional Patent Publication No. 115862/1991 in place of the mixed ferrite-coated magnetic particles of the present invention.

The results are shown in FIG. 1 to FIG. 6 and Table 1.

What is claimed is:

1. A magnetic particle for an immunoassay method, which comprises a core and a coating layer formed on the surface of the core wherein said core comprises an organic polymer matrix and said coating layer comprises a mixed crystal ferrite represented by the formula:

wherein M represents at least one metal selected from the group consisting of manganese, nickel, zinc, cobalt, copper, magnesium, tin, calcium and cadmium, and x is a number satisfying the relation:

0<x<3, and an antigen or an antibody is bound onto the surface of the coating layer and wherein said particle has a particle size of 0.03 to 10 μm.

2. The magnetic particle according to claim 1, wherein said particle has a saturation magnetization of 1 to 60 emu/g.

3. The magnetic particle according to claim 1, wherein said particle is further coated with a polymer and the antigen or the antibody is bound to a layer of said polymer.

4. The magnetic particle according to claim 3, wherein said polymer is selected from the group consisting of a silane polymer, a polyamide and a polystyrene.

5. The magnetic particle according to claim 1, wherein said organic polymer matrix comprises a polymer comprising at least one of a styrene, an acrylate and a methacrylate.

6. The magnetic particle according to claim 1, wherein the coating layer of said particle is formed by a ferrite plating method.

7. The magnetic particle according to claim 4, wherein said silane polymer is a polymer of a silane monomer selected from the group consisting of p-aminophenyltrimethoxysilane, 3-aminopropyltrimethoxysilane, N-2-aminoethyl-3-aminopropyltrimethoxysilane, H$_2$NCH$_2$CH$_2$—NHCH$_2$CH$_2$—NHCH$_2$CH$_2$CH$_2$—Si—(OCH$_3$)$_3$, n-dodecyltriethoxysilane and n-hexyltrimethoxysilane.

8. The magnetic particle according to claim 7, wherein a terminal amino group(s) of the silane polymer is carboxylated by an acid anhydride selected from the group consisting of glutaric anhydride, maleic anhydride and succinic anhydride.

9. An immunoassay method comprising the steps of reacting a specimen containing an antigen with an antibody which specifically binds to said antigen, so as to bind said antigen to said antibody, wherein said antibody is immobilized on the particle of claim 1; measuring an amount of bound antigen; and correlating the amount of the bound antigen obtained in the measuring step with an amount of antigen in a specimen.

10. The immunoassay method according to claim 9, wherein said method is an enzyme-immunoassay method.

11. The immunoassay method according to claim 10 wherein (a) said specimen comprises said antigen; (b) said antibody is immobilized on said particle; and (c) said method further comprises adding an enzyme-labeled antibody, which specifically binds to said antigen in the specimen; and separating unreacted enzyme-labeled antibody from the specimen by washing out said unreacted enzyme-labeled antibody, and adding an enzyme substrate specific for the enzyme and measuring the activity of antibody-bound enzyme.

12. An immunoassay method comprising the steps of reacting a specimen containing an antibody with an antigen which specifically binds to said antibody, so as to bind said antibody to said antigen, wherein said antigen is immobilized on the particle of claim 1; measuring an amount of bound antibody; and correlating the amount of the bound antibody obtained in the measuring step with an amount of antibody in the specimen.

13. The immunoassay method according to claim 12, wherein said method is an enzyme-immunoassay method.

14. The immunoassay method according to claim 13, wherein (a) said specimen comprises said antibody; (b) said antigen is immobilized on said particle; and (c) said method further comprises adding an enzyme-labeled antigen, which specifically binds to said antibody in the specimen; and separating unreacted enzyme-labeled antigen from the specimen by washing out said unreacted enzyme-labeled antigen, adding an enzyme substrate specific for the enzyme and measuring the activity of antigen-bound enzyme.

15. The immunoassay method according to claim 13, wherein (a) said specimen contains said antibody; (b) said antigen is immobilized on said particle; and (c) said method further comprises adding an enzyme-labeled anti-human immunoglobulin antibody which specifically binds to said antibody in the specimen; and separating unreacted enzyme-labeled antibody from the specimen by washing out said unreacted enzyme-labeled antibody, adding an enzyme substrate specific for the enzyme and measuring the activity of antibody-bound enzyme.

* * * * *